(12) United States Patent
Ljungström et al.

(10) Patent No.: US 8,629,761 B2
(45) Date of Patent: Jan. 14, 2014

(54) SELECTION OF AN IMD BY MEANS OF DIRECTIONAL ANTENNA

(75) Inventors: Jan Ljungström, Hässelby (SE); Hans Abrahamson, Stockholm (SE); Leif Lindkvist, Stenhamra (SE); Stefan Wahlberg, Stockholm (SE); Niklas Sköldengen, Täby (SE)

(73) Assignee: St. Jude Medical AB, Jarfalla (SE)

( * ) Notice: Subject to any disclaimer, the term of this patent is extended or adjusted under 35 U.S.C. 154(b) by 546 days.

(21) Appl. No.: 12/516,371

(22) PCT Filed: Nov. 30, 2006

(86) PCT No.: PCT/SE2006/001376
§ 371 (c)(1),
(2), (4) Date: May 27, 2009

(87) PCT Pub. No.: WO2008/066424
PCT Pub. Date: Jun. 5, 2008

(65) Prior Publication Data
US 2010/0066500 A1   Mar. 18, 2010

(51) Int. Cl.
*H04Q 5/22* (2006.01)
*G08B 13/14* (2006.01)
*G08B 17/12* (2006.01)
*G08B 23/00* (2006.01)
*A61N 1/00* (2006.01)
*H01Q 1/12* (2006.01)
*H01Q 3/00* (2006.01)
*H01Q 1/40* (2006.01)

(52) U.S. Cl.
USPC ...... 340/10.1; 340/10.6; 340/572.1; 340/600; 340/573.1; 607/9; 607/32; 607/60; 343/718; 343/720; 343/764; 343/873

(58) Field of Classification Search
USPC ......... 340/10.1–10.6, 572.1–572.8, 600–607, 340/12.52, 5.8, 573.1; 607/2, 9, 60, 32; 343/718, 720, 723, 724, 764, 873, 714
See application file for complete search history.

(56) References Cited

U.S. PATENT DOCUMENTS

| | | |
|---|---|---|
| 5,814,089 A | 9/1998 | Stokes et al. |
| 2003/0093124 A1* | 5/2003 | Sutton ............................... 607/9 |
| 2003/0229382 A1 | 12/2003 | Sun et al. |
| 2004/0106967 A1* | 6/2004 | Von Arx et al. ................. 607/60 |
| 2004/0142696 A1* | 7/2004 | Saunders et al. ............... 455/450 |
| 2004/0171355 A1* | 9/2004 | Yu et al. .......................... 455/78 |
| 2005/0137647 A1 | 6/2005 | Wallace et al. |
| 2006/0020302 A1 | 1/2006 | Torgerson et al. |
| 2006/0020303 A1 | 1/2006 | Torgerson et al. |

(Continued)

*Primary Examiner* — Jennifer Mehmood
*Assistant Examiner* — Mirza Alam

(57) ABSTRACT

In a method and a system for initiating communication with an implantable medical device to conduct a wireless communication session between the implantable medical device and an external programmer device. A directional antenna is employed for initiating communication between a programmer device and an implantable medical device (IMD). The IMD is targeted by the programmer device by having an operator of the programmer device orient the directional antenna toward the IMD and transmitting a communication-initiating signal from the programmer to the IMD via the directional antenna. The directional antenna has a directional characteristic and communication range. the IMD responds to the communication-initiating signal by sending identification information to the programmer. the programmer may then use this identification to establish a communication session with the IMD targeted by the directional antenna.

9 Claims, 5 Drawing Sheets

(56) References Cited

U.S. PATENT DOCUMENTS

| | | | |
|---|---|---|---|
| 2006/0020304 A1* | 1/2006 | Torgerson et al. | 607/60 |
| 2006/0142820 A1* | 6/2006 | Von Arx et al. | 607/60 |
| 2007/0299349 A1* | 12/2007 | Alt et al. | 600/484 |
| 2008/0183247 A1 | 7/2008 | Harding | |

* cited by examiner

SELECTION OF AN IMD BY MEANS OF DIRECTIONAL ANTENNA

BACKGROUND OF THE INVENTION

1. Field of the Invention

The present invention relates to a method and a system for initiating communication with an implantable medical device to conduct a wireless communication session between the implantable medical device and an external (extracorporeal) programmer device.

2. Description of the Prior Art

When communicating with an implantable medical device (IMD) implanted in tissue of a human or animal body, a radio frequency (RF) transceiver is used for wireless communication of signals to/from RF communication circuitry comprised in the IMD. An IMD may be embodied in the form of an implantable cardioverter defibrillator (ICD), a neural simulator, an implantable drug pump, an implantable cardiac monitor or health monitor, a pacemaker, etc. Communication may be established with the IMD for a number of reasons. For instance, medical personnel may want to monitor and/or adjust parameters of the IMD, it may be desirable to perform medical or therapeutic treatment of the body via the IMD, e.g. defibrillation, restart of a stopped heart, injection of an insulin dose, etc. Needless to say, RF signalling enables establishment of a communication channel without having to open up the patient surgically. Hence, an RF device referred to as a programmer is employed to establish RF communication with transceiver circuitry within an IMD. From a user's point of view, a programmer may be viewed upon as a computer arranged with an RF transceiver, a user interface for controlling the programmer and dedicated software designed for the purpose of communicating with an IMD. When establishing communication with an IMD, the programmer broadcasts a wake-up signal to which the IMD responds before a communication session may be undertaken between the programmer and the IMD, i.e. before payload data is exchanged between the programmer and the IMD.

In certain environments, such as in hospitals or other care institutions, a situation may arise where a number of patients carrying IMDs are located within the coverage area (broadcast) of a programmer. When an operator uses the programmer to broadcast an RF wake-up signal for establishing communication with an IMD, it may happen that more than one IMD respond to the broadcast. This multi-device response to a broadcast is problematic for a number of reasons. For instance, a collision of responses may arise in uplink communication from the IMDs to the programmer. Potentially, the established communication channel may fail in case of uplink response collisions. International patent application having publication number WO 2006/014713 discloses a medical system and a method of establishing communication between a plurality of implantable medical devices and an external device by means of an identification command sent transcutaneously to the implantable medical devices. The implantable medical devices respond to the identification command with a response in one of a plurality of time slots. The external device receives the response from each of the implanted medical devices and establishes transcutaneous communication to a selected one of the devices based upon an order in time of which the implanted medical devices respond.

Even though the disclosure of WO 2006/014713 may mitigate problems relating to uplink response collisions, a problem still remains in that a selected response provides the external device with an IMD identifier, but a user of the external device still needs to determine which one of the plurality of physical IMDs located within the communication range of the external device that actually corresponds to the selected response.

SUMMARY OF THE INVENTION

An object of the present invention is thus to solve or at least mitigate the above mentioned problems in prior art and to provide a manner of establishing a communication session between a programmer device and an IMD without having to undertake a tedious, time-consuming and inexact selection and identification process.

A basis of the invention is to employ a directional antenna for initiating communication between a programmer device and an implantable medical device (IMD). To this end, the IMD is targeted by the programmer device by having an operator of the programmer device directing an antenna toward the IMD and transmitting a communication-initiating signal from the programmer to the IMD via the antenna. The antenna is a directional antenna having a certain directional effect and communication range. The IMD responds to the communication-initiating signal by sending identification information to the programmer. The programmer may then use this identification to establish a communication session with the IMD targeted by means of the directional antenna.

The present invention is advantageous for a number of reasons. Since the programmer uses a directional antenna to target the IMD, it will most likely not receive response signals from other IMDs located in the vicinity of the targeted IMD. As a consequence, there will be no collisions in the uplink communication direction, i.e. from the IMD to the programmer. Further, there is no need for an operator to go through a tedious process of having to sort and distinguish a large number of responses, select an IMD identifier and finally associate the selected IMD identifier with a physical IMD within the range of the programmer in order to set up a communication session. However, even if more than one IMD would respond to the communication-initiating signal, it is likely that the number of responding IMDs is small because of the directional effect of the antenna.

Even though an established channel will not necessarily be corrupted by multiple uplink responses, it is desirable for an operator of the programmer to limit the number of responses for practical reasons, if possible down to one single response. Assuming that a prior art programmer is used for communication with IMDs in a storage where a great number of devices, possibly in hundreds, are stocked before being put on the market, a response to a programmer RF broadcast may assume chaotic proportions, in case a great number of IMD responds to the broadcast. Since the identifier of a given IMD is not known in advance, the present invention provides a highly efficient scheme of identifying an IMD for establishing a communication session between the identified IMD an a programmer device.

In an embodiment of the present invention, the IMD towards which the directional antenna is directed is indicated visually, for example by means of a light beam. In a preferred embodiment, light beams are used to indicate the spatial range of the main lobe of the directional antenna.

A situation may arise where the operator of the programmer device directs the antenna in such a manner that it does not unambiguously target a single IMD. Possibly, in such a situation, a plurality of IMDs fall within the communication range of the directional antenna. Thus, in a further embodiment of the present invention, in case the programmer device receives more than one response signal as a result of transmitting the communication-initiating signal, the IMD designated by the identification information of the strongest response signal is selected for further communication. It is then assumed that the selected identification originates from the IMD towards which the directional antenna is directed. Of a plurality of IMDs which are candidates for responding to a communication-initiating signal transmitted by the programmer device, the IMD targeted by the directional antenna is most likely to respond with the strongest signal, since it is located in the main lobe of the directional antenna.

Further features of, and advantages with, the present invention will become apparent when studying the appended claims and the following description. Those skilled in the art realize that different features of the present invention can be combined to create embodiments other than those explicitly described in the following.

DESCRIPTION OF THE PREFERRED EMBODIMENTS

Figure 1:
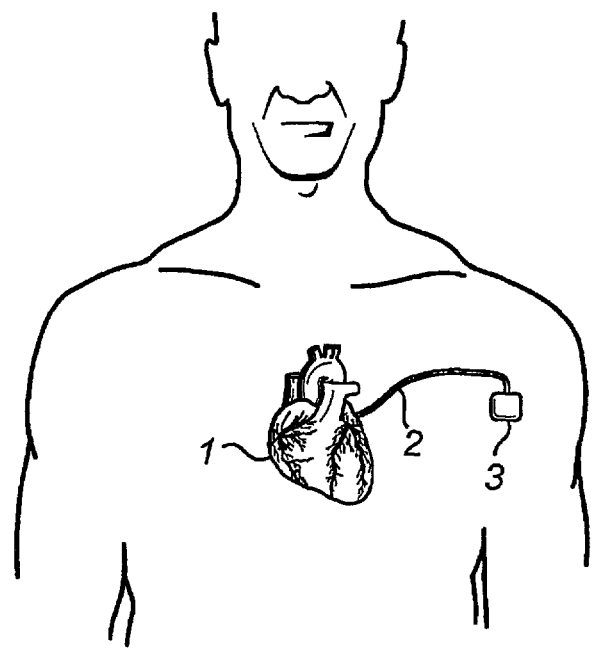
FIG. 1 is a schematic view of a patient's body showing a pacemaker implanted in the body.

FIG. 1 illustrates an implantable medical device (IMD) in the form of a pacemaker 3 implanted in a patient's body. A lead 2 connects the pacemaker 3 to the heart 1, thereby allowing stimulation of the heart 1 and control of the heart rhythm. In order to transmit and receive RF signals, the pacemaker 3 comprises a transceiver and an antenna.

Figure 2:
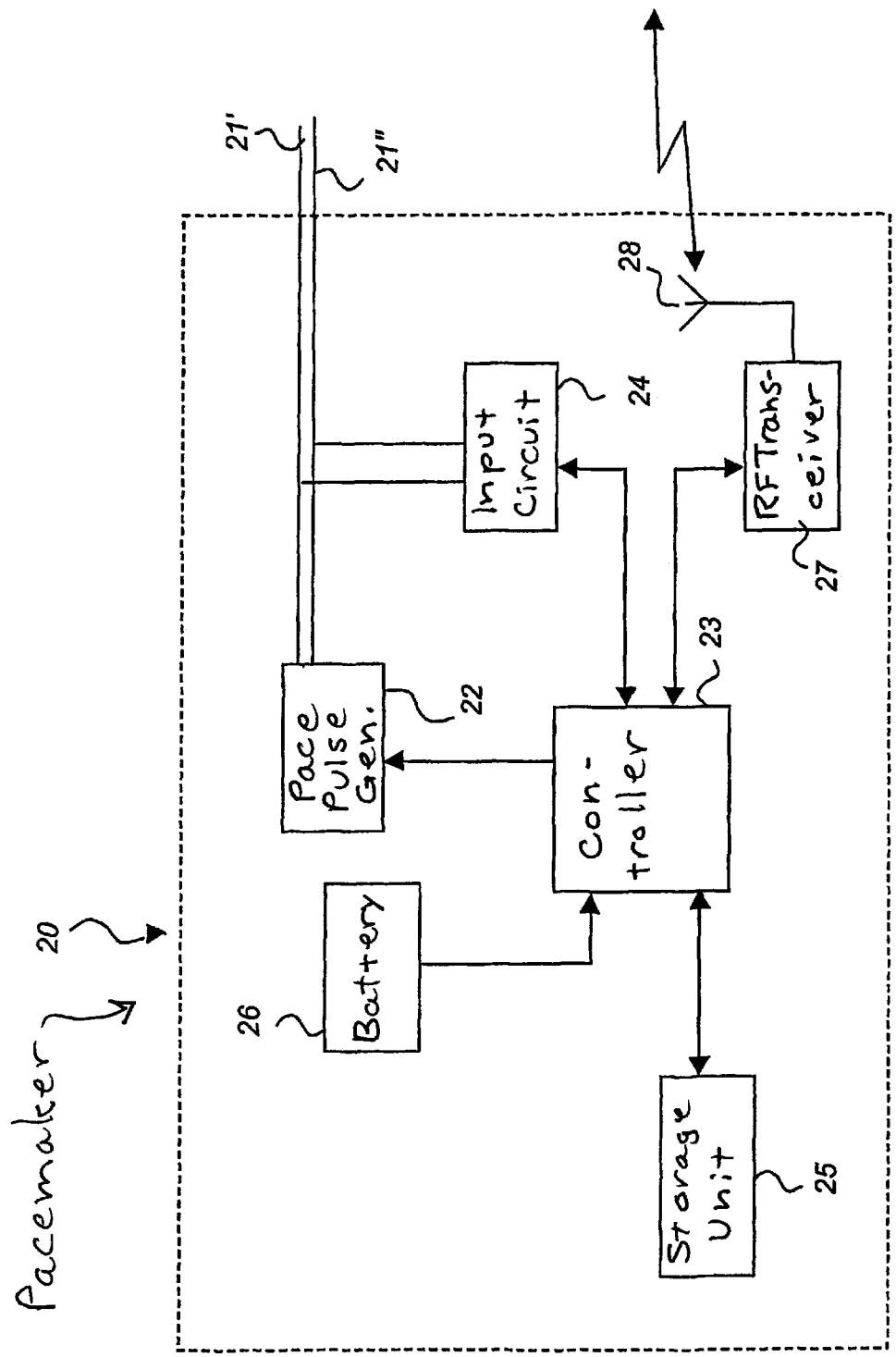
FIG. 2 illustrates functional blocks of an IMD in the form of a pacemaker, to which the present invention may be applied.

FIG. 2 illustrates functional blocks of a pacemaker 20 (in this particular case a bi-ventricular pacemaker) in more detail. The pacemaker 20 has a housing (not shown) being hermetically sealed and biologically inert. Typically, the housing is conductive and may thus serve as an electrode. The pacemaker 20 is connectable to one or more pacemaker leads, with only two shown in FIG. 2; namely a ventricular lead 21' implanted in the right ventricle of the heart and an atrial lead 21" implanted in the right atrium of the heart. The leads 21', 21" carry one or more electrodes, such as a tip electrode or a ring electrode, arranged to, inter alia, measure impedance or transmit pacing pulses for causing depolarization of cardiac tissue adjacent to the electrodes generated by a pace pulse generator 22 operated by a controller or controlling circuit 23 including a microprocessor for e.g. signal processing. The controller 23 controls, inter alia, pace pulse parameters such as output voltage and pulse duration.

Further, a storage unit 25 is connected to the controller 23. The storage unit 25 may include a random access memory (RAM) and/or a non-volatile memory such as a read-only memory (ROM). Detected signals from the patient's heart are processed in an input circuit 24 and are forwarded to the controller 23 for use in logic timing determination in known manner. The pacemaker 20 is powered by a battery 26, which supplies electrical power to all active electrical components of the pacemaker. The pacemaker 20 also has an RF transceiver 27 for wireless communication of signals to/from an external programmer. Medical personnel may e.g. want to monitor and/or adjust parameters of the pacemaker 20 to perform reprogramming. The transceiver is connected to an antenna 28 via which the wireless communication occurs. The pacemaker 20 is typically arranged such that it can register an IEGM and provided to an external programmer via the RF transceiver 27.

Figure 3:
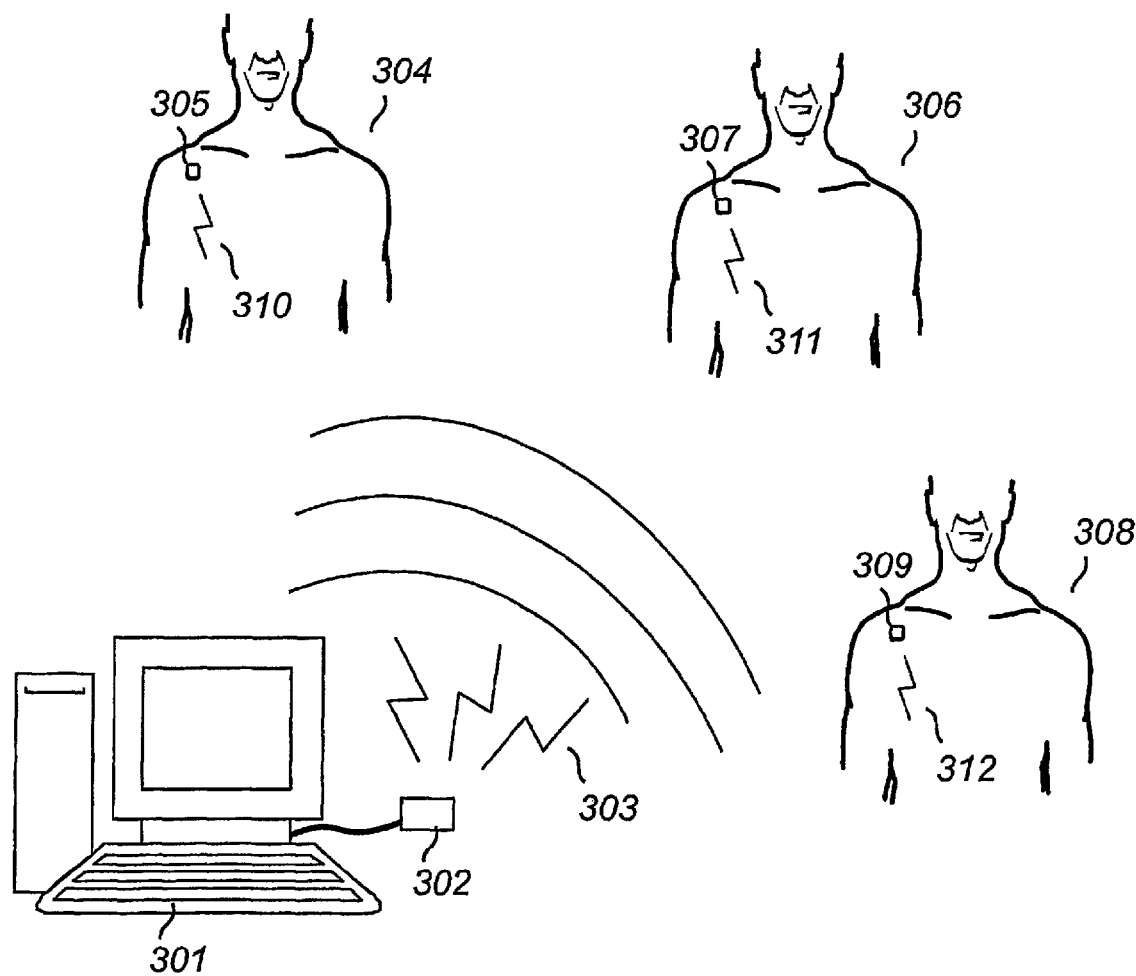
FIG. 3 shows a prior art IMD telemetry system.

A prior art IMD telemetry system is shown in FIG. 3. A programmer device 301 is employed to communicate with transceiver circuitry in IMDs. In principle, a programmer is a computer arranged with an RF transceiver 302 connected to the computer via an appropriate connection such as USB, a user interface for controlling the programmer and dedicated software designed for the purpose of communicating with an IMD. When establishing communication with an IMD, the programmer broadcasts a wake-up signal 303, i.e. a communication-initiating signal, before a communication session can be undertaken and IMDs within communication range of the programmer will respond to the wake-up signal. In this particular example, three patients 304, 306, 308 having a respective pacemaker 305, 307, 309 replies to the wake-up signal by means of transmitting a respective response signal 310, 311, 312 each comprising an identifier for the pacemaker in question. This identifier typically comprises the serial number of the IMD with which it is associated. As has been previously mentioned in connection to discussing prior art, a multi-device response could cause a collision of responses in uplink communication from the pacemakers 305, 307, 309 to the programmer 301. Further, an operator of the programmer still needs to determine from which one of the patients a particular response signal originates, which may be a cumbersome process.

Figure 4:
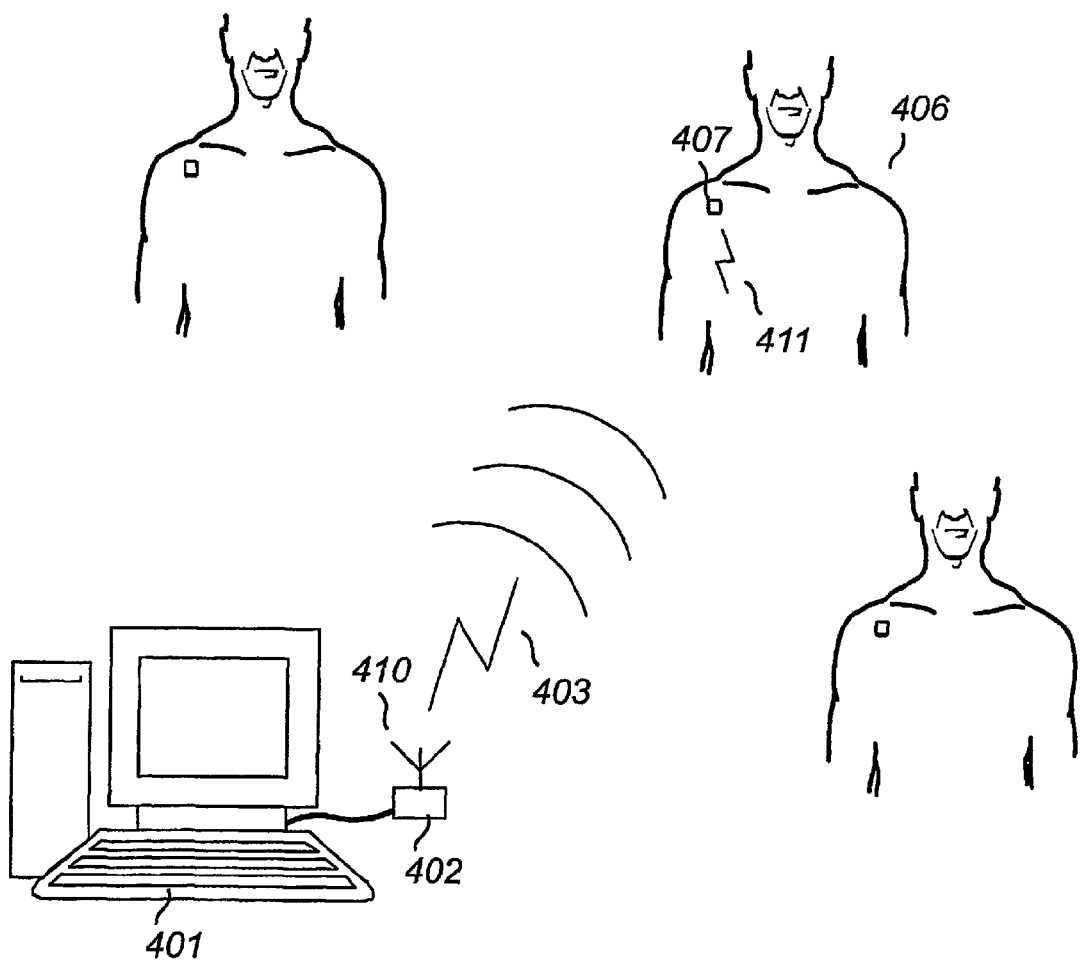
FIG. 4 shows an embodiment of the present invention, in which a directional antenna 410 is directed towards a patient with which a communication session is to be conducted.

With reference to FIG. 4, in an embodiment of the present invention, a directional antenna 410 is oriented so that its spatial directionality pattern is most effectively directed toward the patient 406 with whom a communication session is to be conducted. Then, the communication-initiating signal 403 is transmitted from the programmer device 401 and the RF transceiver 402 to the pacemaker 407 via the directional antenna 410. The pacemaker 407 responds to the wake-up signal 403 by submitting a response signal 411 that contains identification information identifying the implantable medical device in question, i.e. the pacemaker 407. The programmer device 401 can subsequently use the IMD identifier to initiate a communication session with the pacemaker 407. By employing the directional antenna 410, it is possible to target a particular IMD for initiating a communication session. When the particular IMD responds, the operator of the programmer device knows which patient's IMD that is designated by the identifier of the response signal, and there is no need to undertake a time-consuming and tedious identification process for mapping an IMD to a respective patient before communication can be established. Note that the programmer device 401 may receive a response comprising a number of response signals 411 from the pacemaker 407. For instance, it is possible that an IMD transmits a first response signal comprising general information regarding the IMD and a second response signal comprising an IMD identifier.

If a number of IMDs are targeted by the directional antenna, resulting in a corresponding number of response signals received at the programmer device, the programmer device in an embodiment of the invention is provided with a signal discriminator that measures the respective signal strengths of the received response signals. The signal discriminator is arranged, for example, in the actual programmer or at the RF transceiver. Hence, the response signal having the greatest signal strength is considered to be the signal which originates from the IMD targeted by the directional antenna.

Figure 5:
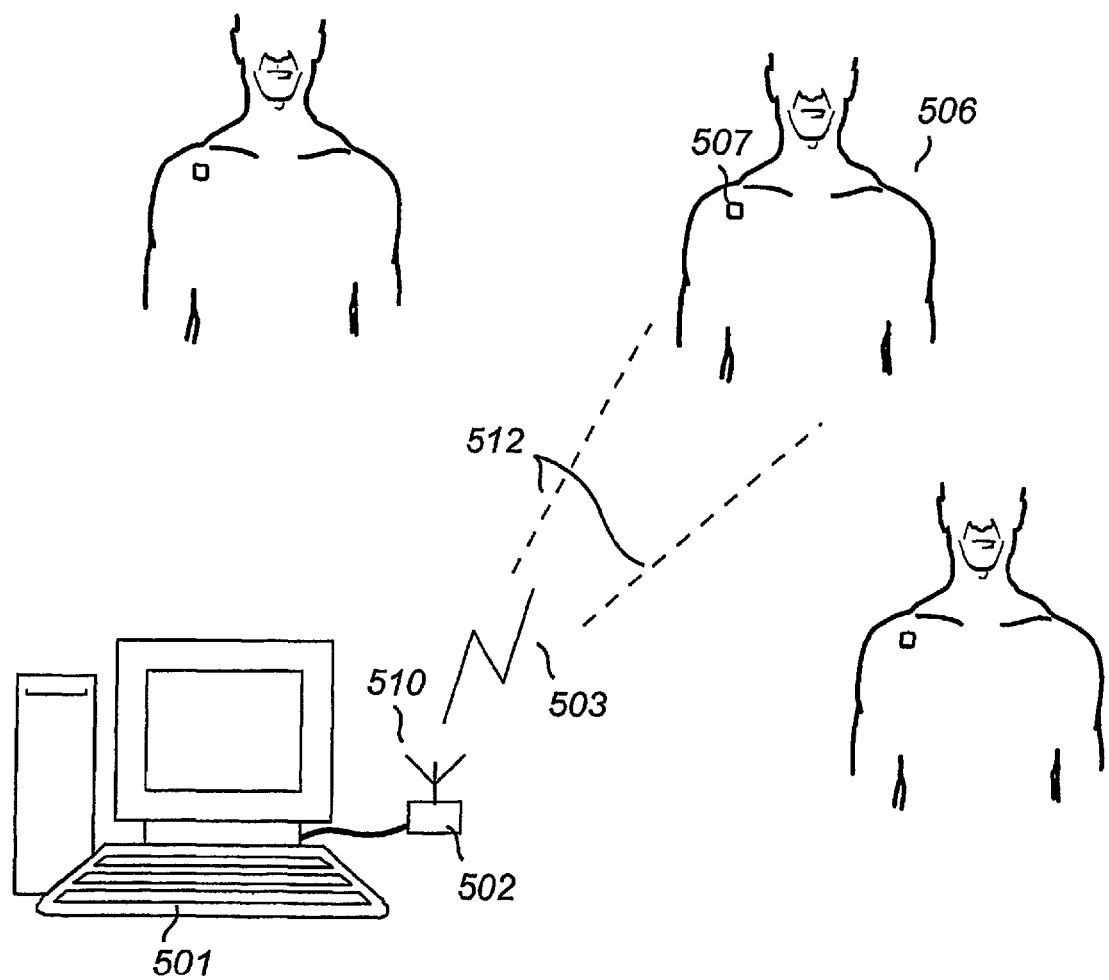
FIG. 5 shows another embodiment of the invention, in which the IMD towards which the directional antenna is directed is visually indicated.

In an embodiment of the invention, which is illustrated in FIG. 5, the IMD 507 toward which the directional antenna 510 is directed is indicated visually, for example by means of one or more light beams 512. In a preferred embodiment, the light beams 512 are used to indicate the main lobe of the directional antenna. Thus, the patient 506 with which communication is established can be visually targeted by an operator of the programmer 501. As a result, the operator can use the light beams 512 as a guiding means for transmitting the wake-up signal 503 via the RF transceiver 502 to the IMD 507.

The programmer device and its RF transceiver shown throughout the drawings typically employs the 402-405 MHz medical implant communication service (MICS) band for bidirectional communication with the IMDs. The MICS standard allows 10 channels, each 300 kHz, to be used in the 402-405 MHz band. Maximum output power is restrained to 25 µW. The IMDs should constantly be enabled, and for the communication-initiating signal (i.e. the wake-up signal), the 2.45 GHz industrial, scientific, and medical (ISM) band is used since less energy is required to communicate in this band. The MICS band support wireless communication having ranges of 2 meters or more. Advantageously, when employing the directional antenna according to embodiments of the present invention, a communication range of several meters is enabled. As an effect, the directional antenna can be located quite a distance from an IMD with which communication is to be established. Furthermore, reception sensitivity is increased at the programmer device, since a directional effect is created between the antenna and the targeted IMD.

Any suitable directional antenna that complies with the employed standard (e.g. MICS) can be used, and a large number of directional antennas are commercially available. In the exemplifying implementation given in the above, the directional antenna may be able to communicate in the MICS band as well as in the 2.45 GHz ISM band. Possibly, the directional antenna 410, 510 of the respective RF transceiver, 402, 502 is embodied in the form of three individual antennas, with two of the antennas being designated for MICS transmission and reception while the third being used for transmission of 2.45 GHz wake-up signals. In a further embodiment, even though three individual antennas are used, only the 2.45 GHz antenna is a directional antenna.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

We claim as our invention:

1. A method of initiating communication with an implantable medical device for conducting a wireless communication session between the implantable medical device and an external programmer device, the method comprising the steps of:

transmitting a communication-initiating signal from said programmer device to the implantable medical device using a directional antenna;

receiving a response at the programmer device from the implantable medical device, said response containing identification information identifying the implantable medical device;

measuring respective strengths of multiple received responses, if more than one response is received;

selecting the implantable medical device designated by the identification information of the response having the strongest signal strength for communication; and initiating the communication session with the selected implantable medical device using a non-directional second antenna.

2. The method according to claim 1, wherein the step of initiating communication further comprises, if more than one response are received at the programmer device selecting the implantable medical device designated by the identification information of the strongest response for communication.

3. The method according to claim 1, further comprising the step of:

visually indicating the implantable medical device towards which the directional antenna is directed.

4. The method according to claim 3, wherein the visual indication indicates a main lobe of the directional antenna.

5. The method according to claim 1, wherein the implantable medical device is a pacemaker.

6. A device for initiating communication with an implantable medical device for conducting a wireless communication session, the device comprising:

a directional antenna adapted to transmit a communication-initiating signal;

a non-directional second antenna;

a radio frequency transceiver;

the transceiver being configured to transmit the communication-initiating signal to the implantable medical device via the directional antenna and to receive a response from the implantable medical device, said response containing identification information identifying the implantable medical device; and a signal processor configured to measure respective strengths of multiple received responses, if more than one response is received, and to select the implantable medical device designated by the identification information of the response having the strongest signal strength for communication wherein the transceiver is further configured to initiate a communication session with the selected implantable medical device using the non-directional antenna.

7. The device according to claim 6, further comprising:

an indicator device visually indicates the implantable medical device toward which the directional antenna is directed.

8. The device according to claim 7, wherein the indicator drive indicates a main lobe of the directional antenna.

9. The device according to claim 6, wherein the directional antenna is configured to operate in the 2.4 GHz band and the non-directional antenna is configured to operate in the medical implant communication service (MICS) band.

* * * * *